(12) United States Patent
Fedder et al.

(10) Patent No.: US 8,471,304 B2
(45) Date of Patent: Jun. 25, 2013

(54) METHOD, APPARATUS, AND SYSTEM FOR MICROMECHANICAL GAS CHEMICAL SENSING CAPACITOR

(75) Inventors: Gary Fedder, Turtle Creek, PA (US); Nathan Lazarus, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 13/152,450

(22) Filed: Jun. 3, 2011

(65) Prior Publication Data
US 2011/0316054 A1   Dec. 29, 2011

Related U.S. Application Data

(60) Provisional application No. 61/396,969, filed on Jun. 4, 2010.

(51) Int. Cl.
*H01L 29/66* (2006.01)

(52) U.S. Cl.
USPC .............................. 257/252; 257/253; 257/414

(58) Field of Classification Search
None
See application file for complete search history.

(56) References Cited

U.S. PATENT DOCUMENTS

| | | | |
|---|---|---|---|
| 4,816,888 A * | 3/1989 | Tanaka et al. | 257/253 |
| 5,970,315 A | 10/1999 | Carley et al. | |
| 6,077,712 A | 6/2000 | Livingston | |
| 6,167,748 B1 | 1/2001 | Britton, Jr. et al. | |
| 6,171,865 B1 | 1/2001 | Weigl et al. | |
| 6,431,005 B1 * | 8/2002 | Delaye | 73/724 |
| 6,523,392 B2 | 2/2003 | Porter et al. | |
| 6,677,227 B2 | 1/2004 | Swenson et al. | |
| 6,812,821 B2 * | 11/2004 | Fujita et al. | 338/34 |
| 6,850,859 B1 | 2/2005 | Schuh | |
| 7,061,061 B2 | 6/2006 | Goodman et al. | |
| 7,207,206 B2 | 4/2007 | Pinnaduwage et al. | |
| 7,338,802 B2 | 3/2008 | Frischauf et al. | |
| 7,344,678 B2 | 3/2008 | Majumdar et al. | |
| 7,395,693 B2 | 7/2008 | Porter et al. | |
| 7,425,749 B2 | 9/2008 | Hartzell et al. | |

(Continued)

FOREIGN PATENT DOCUMENTS

EP   1607739 A1   12/2005

OTHER PUBLICATIONS

Alfeeli et al., Multi-Inlet/Outlet Preconcentrator with 3-D μ-Structures Coated by Inkjet Printing of Tenax TA, Solid-State Sensors, Actuators, and Microsystems Workshop, Jun. 1-5, 2008, pp. 118-121.

(Continued)

*Primary Examiner* — Steven Loke
*Assistant Examiner* — Cuong Nguyen
(74) *Attorney, Agent, or Firm* — The Webb Law Firm

(57) ABSTRACT

A method for fabrication of capacitive environment sensors is provided in which the sensor elements are integrated in a CMOS structure with electronics through the use of complementary metal oxide semiconductor (CMOS) fabrication methods. Also provided are environment sensors fabricated, for example, by the method, and a measurement system using the environment sensors fabricated by the method. The described method includes etching away one of the metal layers in a CMOS chip to create a cavity. This cavity is then filled with an environment-sensitive dielectric material to form a sensing capacitor between plates formed by the metal adhesion layers or an array of contacts from other metal layers of the CMOS structure. This approach provides improved sensing capabilities in a system that is easily manufactured.

17 Claims, 15 Drawing Sheets

(a)

U.S. PATENT DOCUMENTS

| | | | |
|---|---|---|---|
| 7,521,257 | B2 | 4/2009 | Adams et al. |
| 2002/0040598 | A1* | 4/2002 | Sugaya et al. .............. 73/335.02 |
| 2003/0002238 | A1 | 1/2003 | Toyoda |
| 2003/0098695 | A1 | 5/2003 | Hsieh et al. |
| 2006/0237310 | A1 | 10/2006 | Patel et al. |
| 2006/0238290 | A1* | 10/2006 | Arisaka ........................... 338/35 |
| 2007/0194406 | A1 | 8/2007 | Patel et al. |
| 2007/0264741 | A1 | 11/2007 | Patel et al. |

OTHER PUBLICATIONS

Chang et al., Charge-Based Capacitance Measurement for Bias-Dependent Capacitance, IEEE Electron Device Letters, May 2006, pp. 390-392, vol. 27, No. 5.

Dokmeci et al., A High-Sensitivity Polyimide Capacitive Relative Humidity Sensor for Monitoring Anodically Bonded Hermetic Micropackages, Journal of Microelctromechanical Systems, Jun. 2001, pp. 197-204, vol. 10, No. 2.

Fedder et al., Laminated high-aspect-ratio microstructures in a conventional CMOS process, Sensors and Actuators A, 1996, pp. 103-110, vol. 57.

Fedder, MEMS Fabrication, ITC International Test Conference, 2003, pp. 691-698, Paper 27.3.

Fedder, CMOS-Based Sensors, Proceedings of the IEEE Sensors Conference, 2005, pp. 125-128.

Fenner et al., Micromachined Water Vapor Sensors: A Review of Sensing Technologies, IEEE Sensors Journal, Dec. 2001, pp. 309-317, vol. 1, No. 4.

Hierlemann, CMOS-based Chemical Sensors, Advanced Micro and Nanosystems, 2005, 20 pages, vol. 2.

Lazarus et al., CMOS-MEMS Capacitive Humidity Sensor, Journal of Microelectromechanical Systems, Feb. 2010, pp. 183-191, vol. 19, No. 1.

Lazarus et al., Integrated vertical parallel-plate capacitive humidity sensor, J. Micromech. Microeng., 2011, pp. 1-9, vol. 21.

Patel et al., Chemicapacitive microsensors for volatile organic compound detection, Sensors and Actuators B, 2003, pp. 541-553, vol. 96.

Wang et al., Humidity sensors based on silica nanoparticle aerogel thin films, Sensors and Actuators B, 2005, pp. 402-410, vol. 107.

Weiss et al., Inkjet Deposition System With Computer Vision-based Calibration for Targeting Accuracy, Technical Report CMU-RI-TR-06-15, Mar. 2006, pp. 1-12.

Yao et al., A capacitive humidity sensor based on gold-PVA core-shell nanocomposites, Sensors and Actuators B, 2010, pp. 327-333, vol. 145.

\* cited by examiner (a)                    (b)

(a)

Unfilled hole

Filled hole (b)

METHOD, APPARATUS, AND SYSTEM FOR MICROMECHANICAL GAS CHEMICAL SENSING CAPACITOR

CROSS-REFERENCE TO RELATED APPLICATIONS

This application claims the benefit of U.S. Provisional Patent Application 61/396,969, filed Jun. 4, 2010.

STATEMENT REGARDING FEDERALLY-SPONSORED RESEARCH AND DEVELOPMENT

This invention was made with government support under Grant Nos. NIOSH/CDC 200-2002-00528 and AFOSR FA9550-07-1-0245. The government has certain rights in this invention.

This invention relates generally to the field of chemical sensing. In particular, it relates capacitive chemical sensors integrated, for example, into a Complementary Metal Oxide Semiconductor (CMOS) structure or like structure.

Capacitive chemical sensors have traditionally been made by creating a bottom electrode, depositing a sensitive material, and then patterning a set of top electrodes (also referred to herein as conductors). A diagram of this structure 10 is shown in FIG. 1*a*, showing silicon 12 and silicon dioxide 14 substrate layers, electrodes 16 and 17 and chemical-sensitive polymer layer 18. In reference to the Figures, electrodes that are numbered differently refer to opposite conductors (+versus −, as the case may be) in the capacitor structure. The silicon dioxide layer serves as a dielectric, electrically insulating, layer that is not sensitive to exposure to chemicals. Many other insulating materials can serve this purpose. The silicon layer serves as a mechanical substrate. Many other materials can also serve this purpose. This structure has high sensitivity, since all the electric field lines must pass through the sensitive material. Using polyimide polymer, sensitivities reported when this method is applied to humidity sensing are approximately 0.2% change in capacitance for every 1% change in relative humidity. However, this structure is difficult to integrate with testing electronics; placing a sensitive layer between two metal layers requires significant processing beyond conventional CMOS, and has not been successfully demonstrated.

As a result, other capacitive sensors have used an alternative approach, coating interdigitated metal electrodes with a sensitive film. This sensor 20 is shown in FIG. 1*b*, which depicts silicon 22 and silicon dioxide 24 substrate layers, electrodes 26 and 27 and chemical-sensitive polymer 28. This simplifies processing, by eliminating the necessity of having metal above and below the sensitive layer, but at a cost of creating a large, parallel capacitance through the substrate under the electrodes. A technique developed by Seacoast (United States Patent Publication No. 2006/0237310) raises the electrodes on a short vertical post, but vertical posts are also difficult to integrate with CMOS processing.

A variant of this approach, developed by ETH Zurich (European Patent Publication EP 1 607 739 A1), leaves the oxide in the CMOS in place, coating the top surface of a foundry CMOS chip; this simplifies fabrication, but further reduces the sensitivity since the most direct electric field lines pass through the oxide. A simplified diagram of this approach is shown in FIG. 1*c*, depicting a sensor 30, and showing silicon 32 and silicon dioxide 34 substrate layers, along with electrodes 36 and 37 and chemical-sensitive polymer 38. The sensing capacitance of the ETH Zurich device with polyurethane as the sensitive polymer is 1.4 pF in parallel with a substrate capacitance of 6.4 pF. Since 18% of the total capacitance is affected by the analyte, the sensitivity is at most 18% of that of a parallel plate sensor (such as in FIG. 1*a*), or about 0.04% change in capacitance per percent relative humidity.

Another technique that has been used is to remove the underlying substrate, leaving the electrodes on a thin dielectric membrane (United States Patent Publication No. 2003/0002238 A1); a diagram is shown in FIG. 1*d*. In FIG. 1*d*, sensor 40 is shown, along with silicon 42, silicon dioxide 44, electrode 46 and 47 and chemical-sensitive polymer 48 structures. This has the effect of removing the parasitic capacitance between the electrodes and the substrate, but there will still be a parallel capacitance through the non-sensitive dielectric 44 that will degrade the sensitivity. Accordingly, there is a need for improved methods, apparatuses, and systems for capacitance-based gas chemical sensing which reduces parasitic capacitance, increasing miniaturization, while being manufacturable through low cost methods.

SUMMARY

A method of fabricating a chemical sensor utilizing Complementary Metal Oxide Semiconductor (CMOS) fabrication techniques to produce an integrated chemical capacitive sensor into a CMOS structure is described. The method comprises selective etching of the dielectric of the CMOS ("CMOS dielectric") to expose a metal layer within the CMOS electrically connected in series between two other metal layers, etching the metal layer to provide a cavity, and filling the cavity with an environment-sensitive dielectric material. Alternately, the metal layer may comprise a core metal layer disposed between two metal adhesion layers and etching of the metal layer can selectively remove only the core layer or can remove both the core layer and the two metal adhesion layers.

A chemical sensor integrated into a CMOS structure is also described. The chemical sensor comprises a CMOS structure having at least two metal layers and a CMOS dielectric; and at least one environment-sensitive dielectric material layer connected in series between two of the metal layers to produce a capacitor structure. The CMOS structure comprises channels in the CMOS dielectric extending from a surface of the CMOS structure to the environment-sensitive dielectric material layer such that at least a portion of the environment-sensitive dielectric material layer is exposed to the atmosphere or environment. The channels may or may not comprise the environment-sensitive dielectric material. Alternatively, the environment-sensitive dielectric material layer is disposed between two metal adhesion layers, each of which is independently electrically connected to an adjacent metal layer.

A system for environment sensing comprising one or more such environment sensors integrated into a CMOS structure integrated into circuitry for capacitance measurement is also described. In one embodiment, at least a portion of the circuitry for capacitance measurement is integrated into the CMOS structure with the sensors. In one non-limiting embodiment of this system, the circuitry of the CMOS into which the one or more chemical sensors are integrated is a charge-based capacitance measurement (CBCM) circuit.

DETAILED DESCRIPTION

Figure 1:
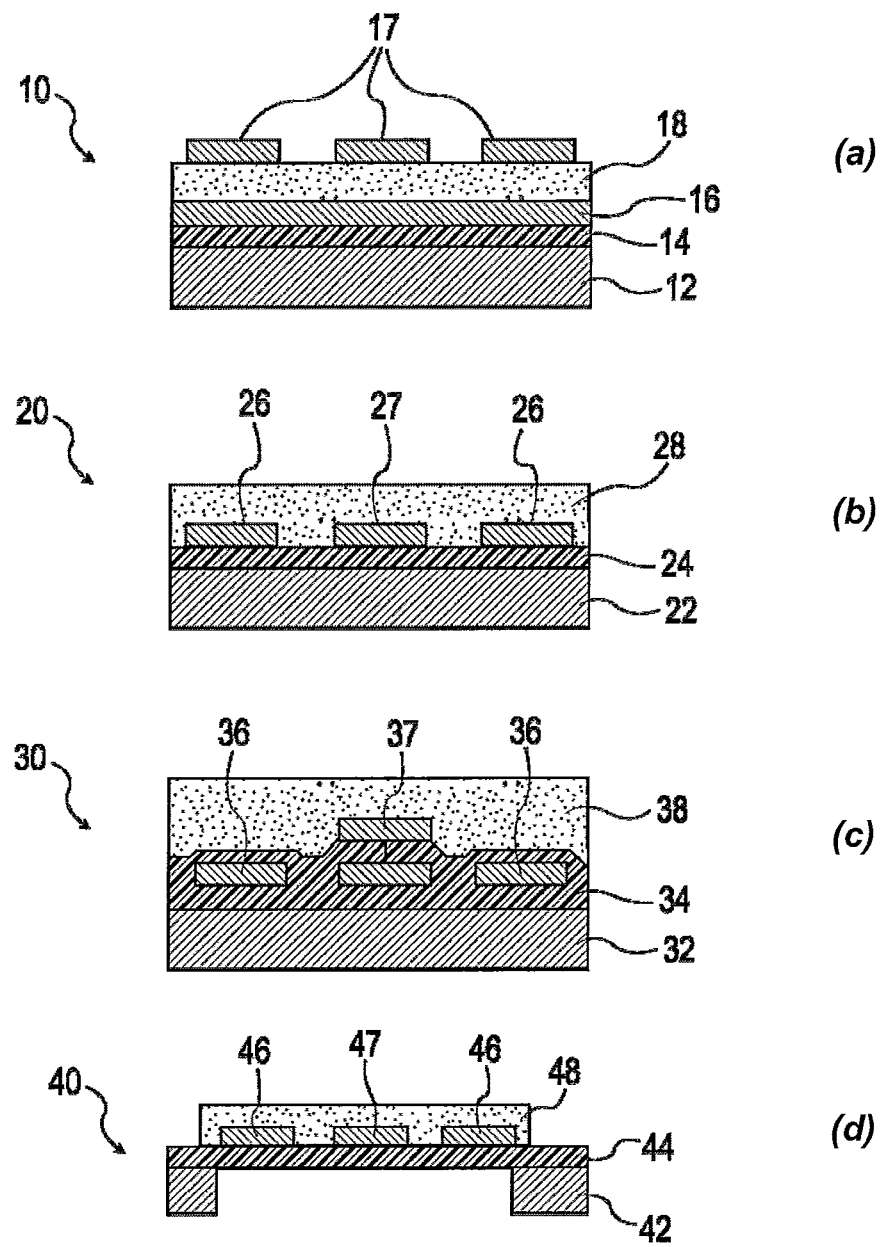
FIG. 1*a* shows a schematic of a prior art capacitive chemical sensor with a sensitized layer on top of the electrodes.
FIG. 1*b* shows a schematic of a prior art capacitive chemical sensor with a sensitized layer between lateral electrodes.
FIG. 1*c* shows a schematic of a prior art capacitive chemical sensor with a sensitized layer between released lateral electrodes.
FIG. 1d shows a schematic of a prior art capacitive chemical sensor with a sensitized layer as a layer between parallel plate electrodes.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

A method for producing an environment-sensitive capacitor (e.g., a parallel-plate capacitor) which is configured into a Complementary Metal Oxide Semiconductor (CMOS) structure. One or more sensor elements are integrated into the CMOS structure through the use of CMOS fabrication methods. Reference is made to the use of the chemical sensor as a humidity sensor, but those skilled in the art will recognize that the chemical sensor represents a general motif that can be applied to many environment sensing applications.

The method, device and systems described herein involve the introduction of an environment-sensitive capacitor into an electronic circuit of a CMOS structure, which is configured to sense a specific analyte. The capacitor uses an environment-sensitive material as a dielectric. According to one embodiment, as the analyte is absorbed into, or otherwise affects the dielectric material, the permittivity of the dielectric material is altered, which raises or lowers the capacitance of the capacitor. By monitoring this change in capacitance, the analyte may be identified or quantified.

In an alternate embodiment, exposure of the environment-sensitive material to the analyte may cause the environment-sensitive material to expand pushing the electrodes of the capacitor apart and changing the capacitance. Again, by monitoring this change in capacitance, the analyte may be identified or quantified.

As used herein, an analyte is any environment parameter that can be measured, including the amount of a particular chemical compound, such as water (humidity), $CO$, $CO_2$, volatile organic compounds (VOCs), and other gases, etc., and a physical parameter, such as temperature. An environment-sensitive dielectric material is not necessarily a traditional dielectric as is used in capacitors, but, as described herein, is a material that changes its permittivity, or otherwise changes the capacitance of the capacitor structure in response to exposure to an analyte.

The structures are described herein as CMOS structures. This is in reference, not to the electronic capabilities of the structure, but with regard to its physical structure and the ability to fabricate the miniaturized analog structures into the CMOS structure, such that additional electronic constituents can be fabricated into the same CMOS structure as the capacitive sensor, including one or more additional capacitive sensors, permitting substantial miniaturization as compared to prior structures which required tie-ins to PC board-mounted electronics. Nevertheless, some variation in the metals and semiconductor materials used in the CMOS device are contemplated, such as the substitution of Cu for Al, the substitution of Ta for Ti/W adhesion layers, or the substitution of $SiO_2$ with, e.g., a low-k dielectric (a low-κ K dielectric, having a dielectric constant, κ, lower than that of $SiO_2$).

Figure 2:
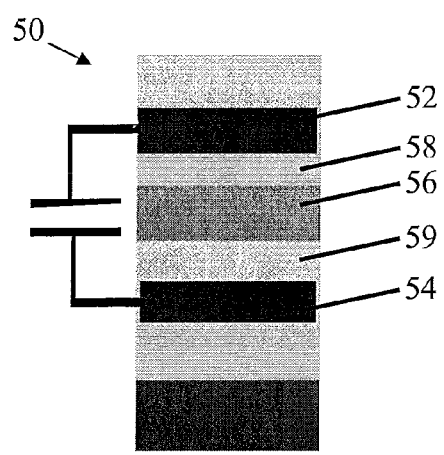
FIG. 2a is a cross sectional diagram showing one option for implementing a vertical parallel-plate chemical sensor into a CMOS by substituting polymer for a metal layer.
FIG. 2b is a cross sectional diagram showing one embodiment of a vertical parallel-plate sensor integrated into a CMOS according to the described method where polymer is substituted for a metal core layer disposed between metal adhesion layers.
Figure 2:
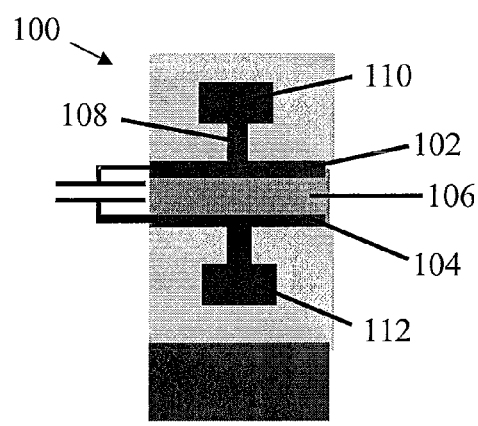

In order to produce an environment-sensitive capacitor in a CMOS stack, conductive layers are provided on either side of a cavity. One such structure 50 is depicted schematically in FIG. 2a. Although the layers are depicted as planar, and planar structures are most typical, other topologies may be utilized. That structure 50 uses two metal layers 52, 54 in the CMOS stack as electrodes while etching the metal layer in between to form the cavity which is then filled with the environment-sensitive dielectric material 56. The capacitance between the two metal layers 52, 54 is then measured to determine amount of the selected chemical that has been absorbed by the environment-sensitive dielectric material 56. The series oxide capacitances 58, 59 that are left above and below the environment-sensitive dielectric material layer 56, due to the inter-metal dielectrics, reduce the sensitivity of the environment-sensitive capacitor. However, as shown in the structure 100 illustrated in FIG. 2b, in many CMOS processes, the metal layers consist of a core metal layer of one composition disposed between two metal adhesion layers 102, 104 of a different composition. In the described method, by using a selective etch that dissolves the core metal layer and not the metal adhesion layers 102, 104, the core metal layer can be removed leaving a cavity between the two metal adhesion layers 102, 104 that is then filled with the environment-sensitive dielectric material 106. The metal adhesion layers 102, 104 act as the top and bottom electrodes of the environment-sensitive capacitor. Metal vias 108 are shown connecting the metal adhesion layers 102, 104 to other metal layers 110, 112 in the CMOS that act as conductive leads to wire the sensor to interface circuitry or connect the capacitor structure to other electronic structures within the same CMOS structure. As would be appreciated by those of skill in the art, in order to effectively integrate a capacitor into an electrical circuit, the electrodes of the capacitor are connected to conductive leads, which in the embodiments described herein are other metal layers of the CMOS stack, but can be integrated by other processes and structures and comprise other structures that are either designed into the CMOS stack before the capacitive sensor structure is formed, or afterwards.

This method of fabricating an environment sensor integrated into a complementary metal oxide semiconductor chip will now be described in more detail. The method described herein, in a general sense, is performed on a CMOS stack that comprises a CMOS dielectric, and in order, and when the CMOS stack comprises a substrate, in order of increasing distance from the substrate, a first metal layer, a second metal layer and a third, discontinuous metal layer, where the second metal layer optionally comprises a core metal layer disposed between two metal adhesion layers. The third metal layer is discontinuous, meaning there are a plurality of (two or more) CMOS dielectric-filled gaps in the layer. The first, second and third metal layers are separated by CMOS dielectric, and according to convention, for example and without limitation, may be described as m1 (metal 1), m2 (metal 2) and m3 (metal 3), respectively, with the first metal layer being at the "bottom" of the CMOS stack and when a substrate is present, closest to the substrate of the CMOS stack, and the third metal layer being at the "top" of the CMOS stack, closest to a surface of the CMOS stack. No directionality or orientation is implied by the designation of a "top" or "bottom", which are only designated as such according to how such structures are typically depicted. Additional metal layers may be present in the CMOS stack, on either side of the first, second and third layers, or even in between the layers, meaning the first, second and third metal layers may be referred to, for example, as m2, m3 and m4, respectively, m3, m4 and m5, respectively, m2, m4 and m5, respectively etc., depending on the configuration of the CMOS stack The first and second metal layers may be continuous or discontinuous. The first and third layers, which may or may not, but typically do, comprise a core metal layer disposed between metal adhesion layers, are independently electrically connected to adjacent metal adhesion layers of the second metal layer using one or more metal conductors, such as vias.

The dielectric of the CMOS stack is etched to provide a channel, and typically two or more channels extending from the surface of the CMOS structure to expose the core metal layer of the target metal layer. Of note, though not necessarily relevant to the methods described herein or the function of the sensor, the second and third metal layers also typically comprise a core metal layer of one composition disposed between two metal adhesion layers of another composition.

Figure 3:
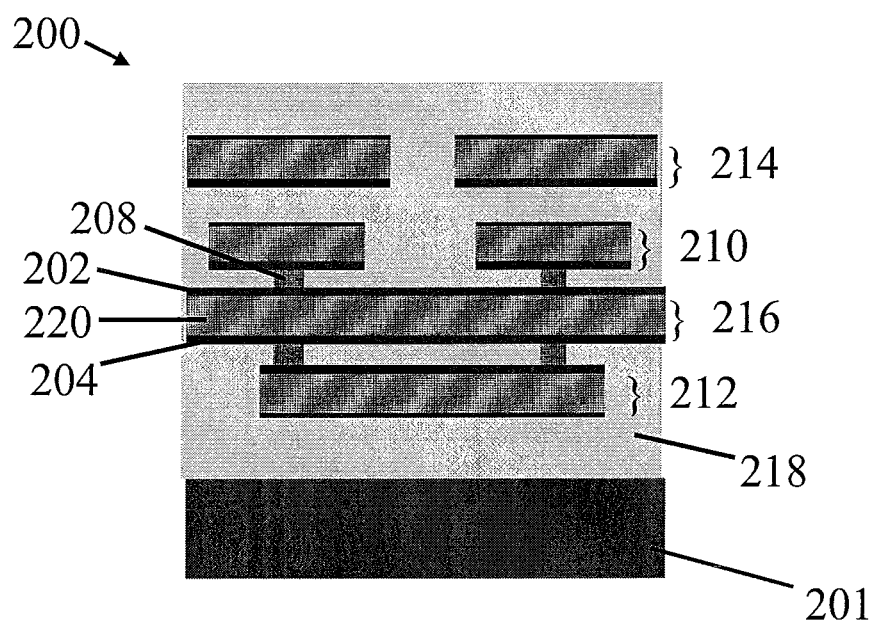
FIG. 3 is a cross section of a typical CMOS useful in the described method, apparatus, and system described herein.
Figure 4:
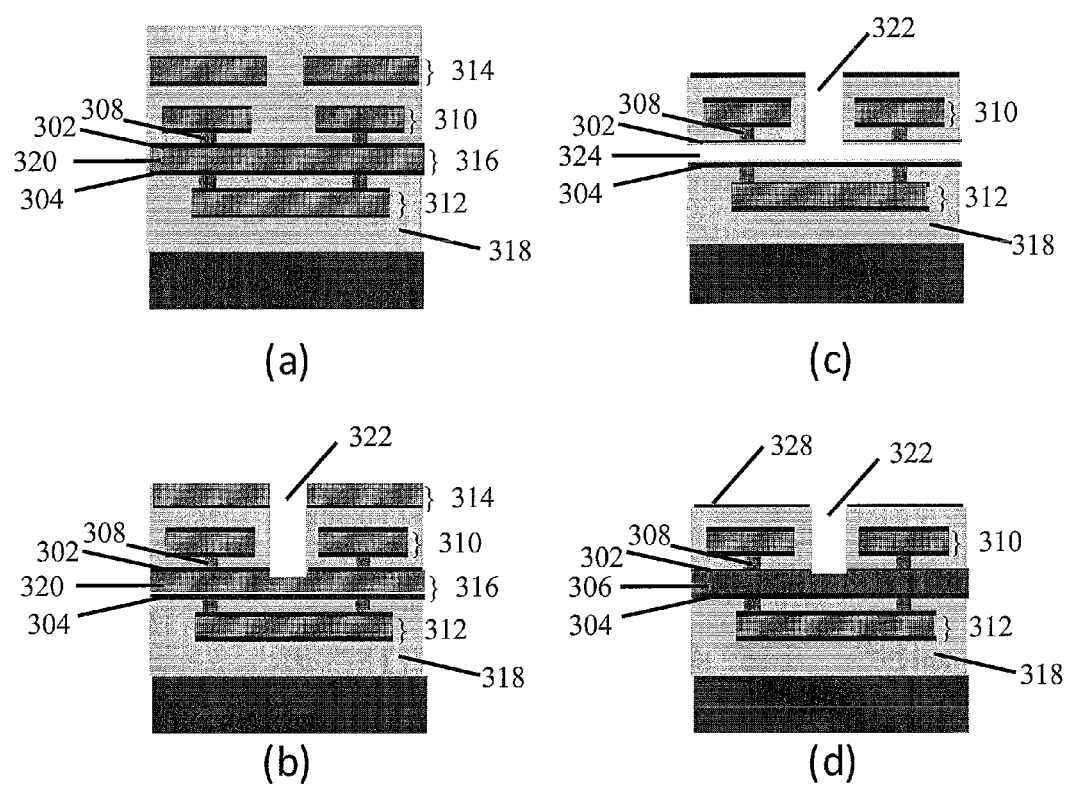
FIGS. 4a-4d show diagrammatically one embodiment of the inventive method for fabricating a chemical sensor integrated into a CMOS.
Figure 5:
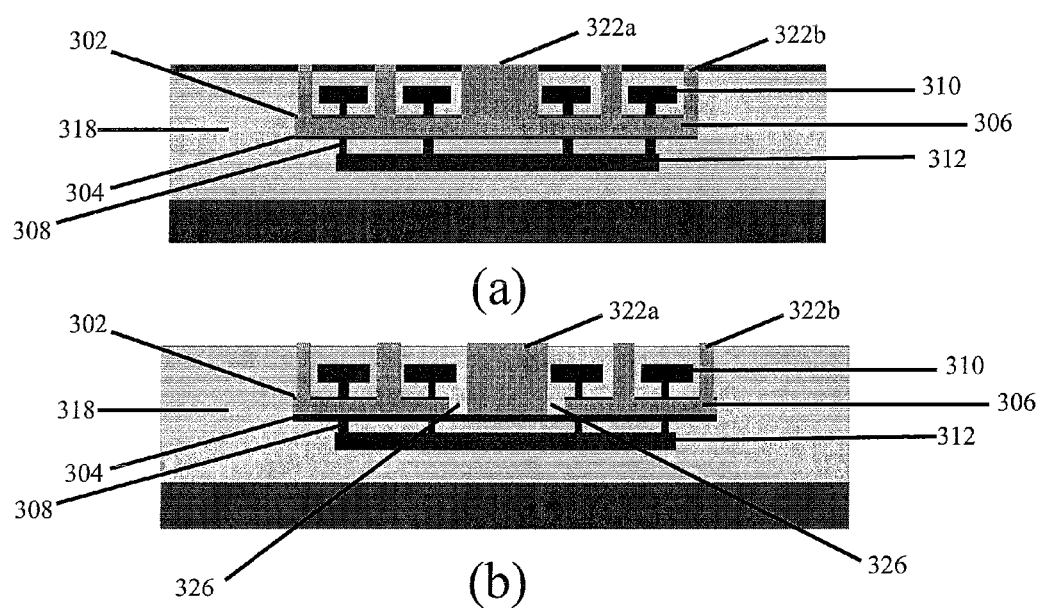
FIGS. 5a and 5b show cross sections of one embodiment of a chemical sensor integrated into a CMOS.

A CMOS structure prepared by any available method, including the Tower/Jazz Semiconductor 0.35 μm process, may be used as a starting material in this process. The metal layer to be converted to a capacitor typically comprises a core metal layer of one composition disposed between two metal adhesion layers of another composition. A CMOS provides a complex electronic circuit contained within a very small area. As an example, as shown in FIG. 3, a typical CMOS stack 200 (chip or otherwise, that is typically commercially available) has several discontinuous metal layers 210, 212, 214, 216 that provide paths for electricity to pass through the electrical circuit contained within the chip. It should be noted that FIGS. 2-5 are schematic in nature and are not in proportion, and also do not depict the entire CMOS stack, but only relevant portions necessary to illustrate the embodiments of the methods and devices described herein. The metal layers 210, 212, 214, 216 are disposed within a matrix of CMOS dielectric 218 and layers 210, 212 and 214 are discontinuous in the sense that they do not cover the same area as continuous metal layers, in that they (in reference to FIGS. 2-5) have lateral gaps of CMOS dielectric that extend through or terminate those metal layers. Metal layer 216, while shown as a continuous layer in FIG. 3, may also be discontinuous. The metal layers 210 and 212 are shown to be electrically-connected to metal layer 216 through metal vias 208 which are metal connections providing a path for the flow of electricity from one metal layer to another. Metal layers 210, 212, 214, 216 of the CMOS structure each comprise a core metal layer 220 of one composition disposed between two metal adhesion layers 202, 204 of another composition. The core metal layer 220 may be of Al metal or alloys, Cu metal or alloys, or any other metal or alloy known to be suitable for use in a CMOS structure as a core metal layer. The adhesion layers 202, 204 may be Ti, W, Ta, or a combination thereof or any other metal or alloy known to be suitable for use in a CMOS as an adhesion layer. The CMOS dielectric 218 may be $SiO_2$ or low-k dielectrics such as Novellus fluorinated oxide (FSG); or other suitable low-k dielectrics, including without limitation fluorine-doped or carbon-doped $SiO_2$.

The CMOS dielectric is selectively etched, for example by anisotropic wet etching or dry etching, to provide at least two channels extending from the surface of the semiconductor to an intermediate target metal layer. Selectively etching provides discrete, specifically placed channels through the CMOS dielectric. The etchant is chosen to only etch the CMOS dielectric and not the metal layers, thus, providing only removal of the CMOS dielectric. The position of the channels can be dictated by the placement of discontinuities in the masking, uppermost metal layer of the CMOS structure, or by any other suitable masking means. In addition to being selective for CMOS dielectric and substantially inert with respect to the metal layers, the etchant is preferably an anisotropic oxide etchant. Anisotropic oxide etchants selectively etch the CMOS dielectric depending on the crystal orientation, etching different crystal orientations at different rates. This effect allows the CMOS dielectric to be etched in substantially one direction, in this case, perpendicular to the metal layers from the surface to the intermediate target metal layer, without substantially etching in other directions, in this case, parallel to the metal layers. An example anisotropic oxide etch is reactive ion etching with a mixture of $CHF_3$ and $O_2$ gases. Etching of the oxide is continued only until the channels extend to expose the core metal layer of the target metal layer. Dry etching methods may be used to produce the passages and expose the core metal layer of the target metal layer, though dry etching processes substantially increase processing costs as compared to wet etching.

Next, the core metal layer is selectively etched, leaving behind a cavity between the metal adhesion layers. The etchant is chosen to only etch the core metal layer and not the metal adhesion layers or the CMOS dielectric, only removing the core metal layer. For an Al core layer and TiW adhesion layers, an example etchant would be Transene Aluminum Etchant A, a mixture containing 80% phosphoric acid, 5% nitric acid, 5% acetic acid and 10% distilled water. For a Cu core layer with tantalum adhesion layers, an example etchant would be nitric acid. In this way, an open cavity is formed between the metal adhesion layers. However, in certain embodiments, the intermediate layer is discontinuous, with CMOS dielectric passing though the metal adhesion layers and the core metal layer such that the CMOS dielectric which fills the discontinuities of the target intermediate metal layer remains creating CMOS dielectric pillars that provide support to help prevent the cavity from collapsing during subsequent processing. By use of the team "pillars" no geometric or topological shape or configuration is implied.

Finally, the cavity between the metal adhesion layers, and optionally the channels in the CMOS dielectric, are filled with an environment-sensitive dielectric material, e.g., capable of selectively absorbing the chemical to be sensed. It should be noted that the sensor will function for certain purposes without filling the cavity, leaving an air-gap as an environment-sensitive dielectric. The environment-sensitive dielectric material is a material for which absorption of or contact with a specific chemical, or exposure to certain physical conditions, alters its permittivity, such that when it is used as a dielectric in a capacitor, the capacitance of the capacitor will be changed depending on the amount of the specific analyte to which the environment-sensitive dielectric material is exposed. By monitoring this change in capacitance, the amount of the specific analyte being sensed can be determined. In this case, the capacitor consists of the metal adhesion layers with the environment-sensitive dielectric material disposed therebetween.

In alternative embodiments, the target metal layer either only comprises a single core metal layer or the etching removes both the core metal layer and the adhesion layers. In these embodiments, the environment-sensitive dielectric material is directly electrically connected to the other metal layers by the metal vias to produce a capacitive sensor.

The systems, apparatuses and devices described herein are fabricated as microfabricated devices (referred to herein as "microdevices" or "microsystems", referring generally to the small size of such systems, devices or apparatuses, and not inferring micrometer-scale or nanometer-scale dimensions). MEMS (microelectromechanical systems) or NEMS (nanoelectromechanical systems), comprising micron- or nanometer-scale mechanical parts/structures) devices are microdevices. Microfabrication methods and compositions useful for preparing the systems, apparatuses and devices described herein are well-known in the MEMS, NEMS, printed-circuit board (PCB) and integrated circuit (IC) manufacturing industries. Microsystems may be manufactured from a variety of materials. Common materials include silicon (e.g. polycrystalline silicon and silicon nitride), glass, carbon (e.g. carbon nanotube and graphene), diamond, polymers and metals. A variety of methods may be used to manufacture the apparatuses (See, e.g., G. Fedder, MEMS Fabrication, in Proceedings of the IEEE International Test Conference (ITC '03), Sep. 30-Oct. 2, 2003, Charlotte, N.C.; H. Baltes, et al., CMOS-MEMS, Wiley-VCH, ISBN 3257310800, January 2005).

The devices described herein can be prepared according to standard MEMS, IC, PCB, etc. design and manufacturing methods and criteria. Electronic circuits can be integrated into the device according to known methods. For example, the CMOS structure as described herein optionally includes circuitry for capacitance measurement, including, for example and without limitation, one or more electrical or electronic elements, such as amplifier(s), preamplifier(s), capacitive divider circuit(s) and capacitive bridge circuit(s). The devices can be packaged in any suitable manner providing for efficacy of the sensors and overall function of the devices.

Thin films are deposited by any of a variety of methods, for example and without limitation: physical vapor deposition (PVD), such as sputtering and evaporation; and chemical deposition, such as chemical vapor deposition (CVD), including low pressure CVD and plasma enhanced CVD, and thermal oxidation. Exemplary methods for patterning such devices include: mask lithography (photolithography), electron beam lithography, ion beam lithography, X-ray lithography, diamond patterning, injection molding, microstereolithography, silicon surface micromachining, high aspect ratio silicon micromachining and silicon bulk micromachining may be utilized.

Structures may be formed by etching, including wet and dry etching methods, which may be isotropic or anisotropic methods. Wet methods include, without limitation: acid etching (e.g., with hydrofluoric, nitric, and/or hydrochloric acids), peroxide etching, basic etching (e.g., with potassium hydroxide) and electrochemical etching. Dry etching methods include, without limitation: vapor etching, including xenon difluoride etching, plasma etching, including reactive ion etching and deep reactive ion etching (e.g., etching of silicon-on-insulator (SOI) and epitaxial silicon and single crystal reactive etch and metallization (SCREAM) methods). CMOS structures/processes may be utilized in conjunction with the MEMS manufacturing methods listed above (see, e.g., G. Fedder, CMOS Based Sensors, in Proceedings of the IEEE Sensors Conference (IEEE Sensors '05), pp. 125-128, Oct. 31-Nov. 3, 2005, Irvine, Calif. and G. K. Fedder, Sensors & Actuators A, vol. 57, no. 2, pp. 103-110, November 1996). Both wet and dry etching methods may be isotropic or anisotropic.

Inkjet printing, for example inkjet printing methods using polymer dissolved in solvent, also can be used to deposit and pattern films (see, e.g., Alfeeli B., et al. Solid State Sensors, Actuators and Microsystems Workshop Hilton Head Island, S.C., Jun. 1-5, 2008, pages 118-121, for inkjet deposition of Tenax TA). Given the significant number of materials, methods and structural/topological variations possible, a person of skill in the field of microfabrication of microdevices (e.g., MEMS, NEMS and IC devices) may use any of a variety of methods and materials to produce/manufacture the microdevices described herein. U.S. Pat. Nos. 6,171,865, 6,850,859, 7,061,061 and 7,338,802, each of which is incorporated herein by reference for its technical disclosure, describe MEMS sensor systems, methods of manufacturing such systems, implementation and use of such systems.

Environment-sensitive dielectric material can be added by using a custom drop-on-demand inkjet system (L. Weiss, et al. Inkjet deposition system with computer vision-based calibration for targeting accuracy, Technical report CMU-RI-TR-06-15, Carnegie Mellon University, March, 2006) to deposit the polymer in solution. As would be appreciated by those of ordinary skill in the art of CMOS fabrication techniques and, more generally, semiconductor structure fabrication techniques, the manufacturing steps may include additional steps, and further, identical and substantially or essentially identical structures may be fabricated by a variety of methods, which would become apparent in light of the teachings of this disclosure.

The environment-sensitive dielectric material may be a chemically sensitive polymer or may be a non-polymer. Chemically sensitive polymers can be used to detect most volatile and semi-volatile compounds including industrial solvents, liquid fuels, many chemical warfare agents, and certain volatile compounds present in commercial explosives. In addition, polymer-based sensors have been used to detect several non-VOC compounds, including water vapor and ammonia. The utilized environment-sensitive dielectric materials can more broadly include any substance that can be delivered within a solvent or made into a low viscosity solution and thus wicked in between the metal adhesion layers surrounding the cavity. Some examples other than polymers include nanoparticles (functionalized or non-functionalized) suspended in solution, sol-gel materials and dielectric oils.

A large number of polymers, including polyimide, polymethyl methacrylate (PMMA), poly(ethylene teraphthalate) (PET), polysulfone (PSF), cellulose acetate butyrate (CAB), polyethynyl fluorenol (PEFI), have been used for humidity application. Polymers may be selected for their ability to selectively form weak reversible chemical interactions (hydrogen bonds, van der Waals bonds, and dipole-dipole interactions) with a particular analyte. Liquid polymers or polymers with a low modulus of elasticity may be preferred in certain instances because they absorb analytes more quickly than rigid polymers (S. V. Patel et al. Chemicapacitive microsensors for volatile organic compound detection Sensors and Actuators B 96 (2003) 541-553). Polymers may be chosen based on the findings in the literature applying solubility parameters. Other factors in choosing the polymers include stability, ease of acquisition, solubility in a suitable solvent and ease of coating application (S. V. Patel et al. *Sensors and Actuators B* 96 (2003) 541-553). U.S. Pat. No. 5,970,315, incorporated herein by reference for its technical disclosure, also provides a list of analytes some polymers are sensitive to.

As an example, the fluoroalcohol SXFA has an affinity for hydrogen-bonding bases and is useful for the detection of chemical warfare agents, such as Sarin. Dicyanoallyl silicone (e.g., OV-275, 20,000 cSt) and cyanopropyl methyl phenylmethyl silicone (e.g., OV-225, 9,000 cSt), are siloxane-based compositions that can be used to detect byproducts and impurities found in explosives. Polyethylene-co-vinylacetate (PEVA, e.g., 40% acetate content), polyepichlorohydrin (PECH, e.g., 700,000 MW), polycarbonate urethane (PCUT), polyisobutylene (PIB, e.g., 1350 MW), and polydimethyl siloxane (PDMS, e.g., 100,000 cSt (centistokes)) may be used to detect volatile organic compounds (VOCs) with moderate to low polarity values (S. V. Patel et al. Sensors and Actuators B 96 (2003) 541-553). Other useful polymeric materials include, poly(dimethyl siloxane (PDMS) and poly(etherurethane) (PEUT).

Nanocomposites, such as nanocluster and nanocrystalline materials, also are useful as chemical-sensitive dielectric materials in the capacitor devices described herein. Nanocomposites contain nanometer-sized (e.g. 1-100 nm in at least one dimension) particles of any suitable morphology, such as metallic or ceramic particles. Examples of suitable nanocluster materials include, without limitation, silicon nanoclusters, metal nanoclusters and gold nanoclusters. Nanoclusters and nanoparticles can be capped with a variety of thiol groups, for example that contain alkane, alkene or other carbon containing moiety. In one example, Wei Yao, et al. disclose a Gold-PVA nanocomposite that is useful for moisture sensing. (A capacitive humidity sensor based on gold-PVA core-shell nanocomposites Sensors and Actuators B 145 (2010) 327-333). In another example, silica nanoparticle compositions, such as mesoporous silica (e.g. 2-50 nm pore diameter) or aerogels, have found use as chemical-sensitive dielectric materials in capacitance sensors for detecting humidity and VOCs. An aerogel is a mesoporous ceramic material. Silica in the form of aerogel has a highly porous structure mainly consisting of mesopores supported by a nanoparticle cross-linking framework (Chien-Tsung Wang et al. Humidity sensors based on silica nanoparticle aerogel thin films Sensors and Actuators B 107 (2005) 402-410).

Non-limiting examples of environment-sensitive dielectric materials include: polyimide, polyisobutylene, polydimethyl siloxane, polycarbonate urethane, polyethylene-co-vinylacetate, siloxanefluoro alcohol, polyepichlorohydrine, cyanopropyl methyl phenylylmethyl silicone, and dicyanoallyl silicone.

Also provided herein is a CMOS-based sensor, fabricated by the methods described herein or otherwise. The sensor comprises, a first metal layer; a second layer comprising an environment-sensitive dielectric material; a third metal layer, wherein the first and third metal layers are electrically connected to the environment-sensitive dielectric material, producing a capacitive sensor; and one or more passages extending from an outer surface of the sensor to the second layer, wherein the one or more capacitive environment sensors are integrated into circuitry for capacitance measurement. The environment-sensitive dielectric material layer is optionally disposed between two metal adhesion layers (that is, derived from adhesion layers of a CMOS stack). The first and third metal layers are electrically connected either to the environment-sensitive dielectric material or, when present, to an adjacent metal layer of the second layer to form a capacitive sensor (meaning the first and third layers are not directly connected to each other, but connect to structures, such as vias or metal adhesion layers in contact with the environment-sensitive dielectric material and which serve as electrodes of a capacitor). The sensor comprises one or more passages extending from an outer surface of the sensor to the environment-sensitive dielectric material layer. All of the features of this chemical sensor have been described above.

As described above, in one embodiment, the metal adhesion layers is absent from the second layer, and the environment-sensitive dielectric material layer is then directly electrically connected to each of the first and third metal layers by metal vias.

A system for environment sensing also is provided having one or more chemical sensors integrated into a complementary metal oxide semiconductor structure. The system comprises a capacitive sensor, according to any embodiment described herein, incorporated into electronic circuitry that supports the sensor in its use (circuitry for capacitance measurement). More than one capacitive sensor and/or elements of the circuitry for capacitance measurement are integrated into the same CMOS structure as the capacitive sensor according to certain embodiments. In one example, the circuitry into which the one or more chemical sensors are integrated is a charge-based capacitance measurement (CBCM) circuit (See, e.g., Y. Chang, Y., et al. Charge-Based Capacitance Measurement for Bias-Dependent Capacitance, IEEE Electron Device Letters, Vol. 27, No. 5, May 2006, pp. 390-392).

In one embodiment of the described method, the fabrication of the CMOS with an integrated chemical sensor begins with a CMOS chip having at least three discontinuous metal layers 310, 312, 314, 316 as shown in FIG. 4a. The metal layers are composed of a core metal layer 320 disposed between two metal adhesion layers 302, 304. In this non-limiting embodiment, the CMOS chip may be fabricated using the Tower/Jazz Semiconductor 0.35 μm process or any process capable of producing a CMOS chip having at least three metal layers composed of a core metal layer disposed between two metal adhesion layers. As shown in FIG. 4b, an anisotropic oxide etch capable of dissolving the CMOS dielectric 318 is used to selectively etch channels 322 into the CMOS dielectric 318 that extend to an intermediate metal layer 316 in the CMOS that is connected in series between two other metal layers 310, 312 by metal vias 308. The channels 322 are placed such that they do not pass through any metal layers and are etched to a depth that just exposes the top of the intermediate metal layer 316. The channels 322 may appear as a series of holes on the surface of the CMOS chip and may be of uniform size or differ in size. This selective etching of the channels 322 may be accomplished by using the top-most metal layer as an etch mask, defining the channels in the CMOS dielectric.

As shown in FIG. 4c, after the channels have been placed in the CMOS chip, an etchant chosen to selectively dissolve the core metal 320 while leaving the metal adhesion layers 302, 304 intact is injected into at least one of the channels 322 and the core metal 320 is dissolved from the intermediate metal layer 316 forming a cavity 324. A photoresist, for example, Clariant AZ-4210, is used to protect the exposed core metal pads (not shown) at the surface of the CMOS from being dissolved during this process. Metal layer 310 and metal layer 312 are enclosed within the CMOS dielectric 318 defined by metal layer 314, and are not exposed to the etchant. The chip is rinsed in de-ionized water followed by successive rinses in acetone and methanol to prevent surface tension from pulling the capacitor plates (metal adhesion layers 302, 304) closed.

FIGS. 5a and 5b are schematic drawings showing two different expanded cross-sections of a CMOS capacitive sensor structure made according to the described method wherein the intermediate metal layer was also discontinuous. Reference numbers are the same as in FIG. 4. As shown in the cross-section of FIG. 5b, because the intermediate metal layer in the CMOS is discontinuous and the discontinuities are filled with the CMOS dielectric 318, CMOS dielectric pillars 326 will be left in the cavity 324 formed when the core metal 320 has be removed from intermediate metal layer 316. These CMOS dielectric pillars 326 provide support for the cavity 324. The CMOS can be designed such that the discontinuities are specifically located to create CMOS dielectric pillars 326 in specific locations of the CMOS to provide the necessary support to keep the cavity 324 open, for example, in the areas about a periphery of at least one of the channels 322.

As shown in FIG. 4d, an environment-sensitive dielectric material 306 is then injected, wicked or otherwise deposited into at least one of the channels 322 until the cavity 324 formed by the removal of the core metal 320 and, optionally the channels 322, are filled with the environment-sensitive dielectric material 306 such that at least a portion of the environment-sensitive dielectric material 306 is exposed to the atmosphere that the chemically sensitive capacitor will be used to analyze through the channels 322, which extend to the outer surface 328 of the structure.

Figure 6:
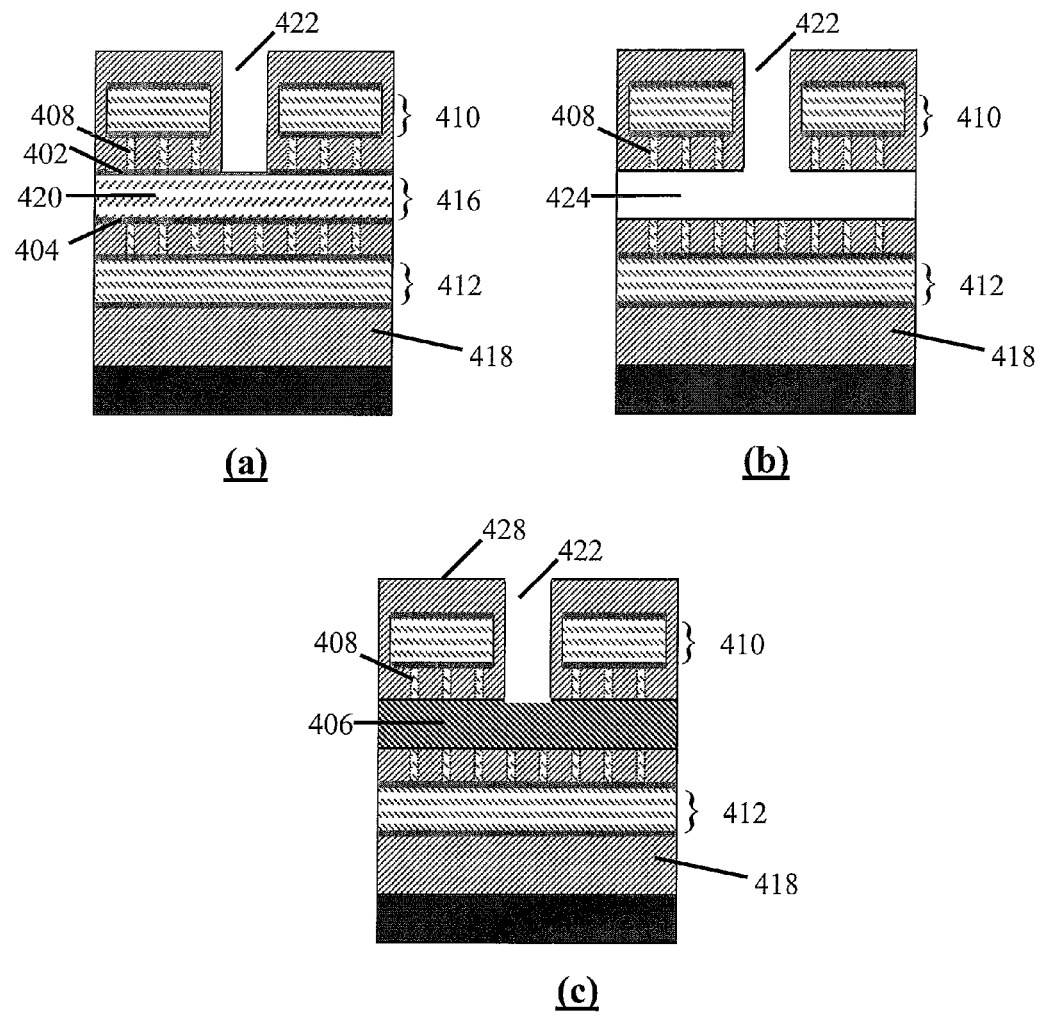
FIG. 6a-6c show diagrammatically another embodiment of the inventive method for fabricating a chemical sensor integrated into a CMOS.

In an alternative embodiment of the described method, shown schematically in FIG. 6, the fabrication of the CMOS structure with an integrated chemical sensor begins with a CMOS chip having at least three metal layers 410, 412, 416. FIGS. 6a, b and c depict only a portion of a larger CMOS structure. In those figures, metal layer 410 is depicted as discontinuous. Metal layers 412 and 416, while depicted as continuous to the extent of the portion of the CMOS structure shown, may be continuous or discontinuous. The intermediate metal layer 416 is electrically connected to metal layers 410, 412 disposed on opposite sides of intermediate metal layer 416 by an array (large number) of metal vias 408. The metal layers are composed of a core metal layer 420 disposed between two metal adhesion layers 402, 404. As shown in FIG. 6a, an anisotropic oxide etch capable of removing the CMOS dielectric 418 is used to selectively etch channels 422 into the CMOS dielectric 418 that extend to the intermediate metal layer 416.

As shown in FIG. 6b, after the channels 422 have been placed in the CMOS chip, an etchant is used to selectively dissolve both the core metal 420 and the metal adhesion layers 402, 404 forming a cavity 424. The chip is rinsed in de-ionized water followed by successive rinses in acetone and methanol.

As shown in FIG. 6c, an environment-sensitive dielectric material 406 is then injected, wicked or otherwise deposited into at least one of the channels 422 until the cavity 424 formed by the removal of metal layer 416 and, optionally the channels 422, are filled with the environment-sensitive dielectric material 406 such that at least a portion of the environment-sensitive dielectric material 406 is exposed to the atmosphere that the chemically sensitive capacitor will be used to analyze through the channels 422, which extend to the outer surface 428 of the structure. Although the devices depicted in FIGS. 2-6 depict a substrate the bottom-most layer, e.g., reference number 201 in FIG. 3—the substrate is an optional component, though it is common in CMOS structures.

It will be recognized that the procedure described above can also be utilized with a CMOS having metal layers with no metal adhesion layers.

More than one chemical sensor, for example and without limitation one or more additional capacitive sensors as described herein, can be integrated into the same CMOS structure. The sensors described herein can be used for any environmental testing, so long as the capacitance of the sensor changes over time with exposure to an environmental condition, such as humidity, temperature, chemicals, $CO_2$, etc. The device may be used to sense chemical(s) within a mask, such as a breathing mask, a gas mask or a respirator.

The devices described herein can be prepared according to standard MEMS, IC, PCB, etc. design and manufacturing methods and criteria. Electronic circuits can be integrated into the device according to known methods. The devices can be packaged in any suitable manner providing for efficacy of the sensors and overall function of the devices. As should be recognized by those of ordinary skill in the art, considerable variation in the layout and components of such a device would result in equivalent functionality.

Figure 7:
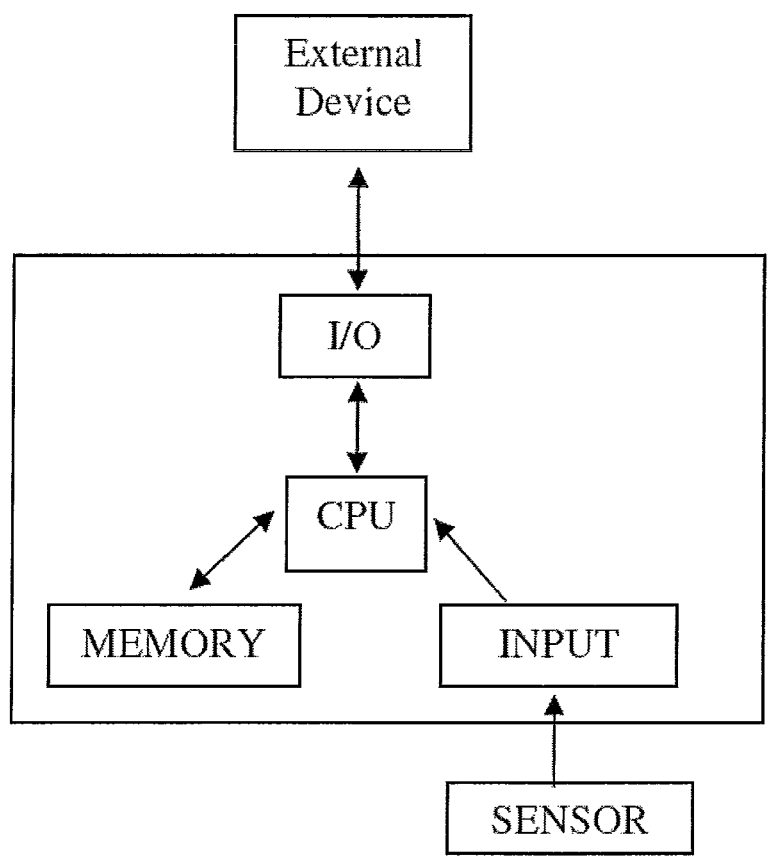
FIG. 7 illustrates one embodiment of a computer system for use in implementing the sensor described herein.

FIG. 7 illustrates one embodiment of a computer system for use in implementing the sensor described above. The capacitive sensors described herein will comprise sufficient electronic circuitry to permit its intended use. At a minimum, and in reference to FIG. 7, electric leads are connected to the capacitor structures and to an "INPUT" of a sensor computing device. The "INPUT" of sensor computing device may comprise one or both of an amplifier (e.g., operational amplifier, preamplifier, differential amplifier, etc.) to amplify signal from the sensors and an analog-to-digital chip/circuit to convert raw analog data obtained from sensors to a digital format. Signal received from sensors is optionally converted to a digital signal, but conversion to a digital signal may be preferred in certain embodiments.

The "CONTROL" of sensor computing device comprises computer software ("software" (or computer software) includes, without limitation: application software, middleware, computer processes, programming languages, code, system software, operating systems, testware, firmware, device drivers, programming tools, data, etc. for carrying out a specific task) and/or computer hardware. Useful computer software and/or hardware constituents are readily developed by those of ordinary skill in the related arts, such as using assembly language on a microcontroller, or using any of a large variety of available programming resources, languages, for example and without limitation: C, Matlab and Java.

The sensor computing device comprises a central processing unit ("CPU") and "MEMORY" which stores data collected and any useful computer software (e.g. firmware) for obtaining, converting, analyzing, storing and uploading data. Memory may comprise of any useful data storage device, including ROM, PROM, FPROM, OTP NVM, RAM, EEPROM, flash memory, etc. Because the device in many instances is miniaturized, the memory component is, to the extent possible, miniaturized. The CPU can comprise of any useful processing circuitry, chip (microprocessor)/hardware/software, combinations etc. The sensor computing device also typically comprises an input/output interface ("I/O" or communications interface), such as a wired interface such as a such as a USB (e.g., USB 2.0), Ethernet, serial (e.g. RS232), GPIB (General Purpose Interface Bus, e.g. IEEE-488), or firewire interface, or a wireless interface, such as an IEEE 802.11 (e.g., 802.11(a), 802.11(b), 802.11(g) or 802.11(n) interface), a Bluetooth interface or an RFID-based interface for communicating with an external device, which can be a second computing device (e.g., PC, laptop, smartphone, PDA, tablet PC, iPad, etc.) for uploading data, analyzing data, outputting data, downloading firmware to the device, or for any activity. Device can be powered by batteries, such as rechargeable batteries (e.g., via a USB interface) or any suitable power source.

The sensors described herein are suitable for use in a remote sensor, such as for monitoring analyte levels in a gas mask or filtration device to determine the presence of environmental contamination, the status of adsorbent levels in the mask (indicating breakthrough of, e.g., VOCs), or to monitor a subject's respiration. As such, the miniaturized device can be installed in a gas mask, and analyte levels can be monitored in the manner indicated and the results stored within the system memory. Periodically or continually the data can be uploaded to an external computing device for monitoring, analysis, storage, etc.

Signal received from sensors is optionally converted to a digital signal, but conversion to a digital signal may be preferred in certain embodiments. In certain embodiments, the signal from sensor is compared to stored data by differencing the output of the sensor either by analog or digital processing. Where data is obtained remotely and transferred to a second computer, the differencing or other comparison methods can be performed either at the sensor computing device or external device. It may in many instances be in such a configuration to conduct the differencing at the sensor computing device, though if a real-time connection (typically wireless, including substantially real-time connection, meaning that data is transferred from the sensor device to the external device regularly, such as every second, 10 seconds, minute or even hourly or daily depending on system tolerances) between the sensor and external device is used, differencing and comparison against reference data, if used, can be conducted in one or both of the sensor and external devices in a stand-alone or distributed manner Alarm functions, indicative of analyte levels reaching a desired threshold, may be programmed or otherwise incorporated into the devices described herein to provide a discernable signal indicating crossing of a threshold. One non-limiting example of such a threshold is an increase in analyte concentrations in a gas sample indicative of VOC breakthrough in a gas mask indicative of loss of function of an adsorbent material in the gas mask.

EXAMPLE

A 300 μm diameter circular parallel-plate sensor was designed and fabricated using the method described above. The starting CMOS had four metal layers 310, 312, 314, 316, as shown in FIG. 4*a* and was fabricated using the Tower/Jazz Semiconductor 0.35 μm process. In reference to FIG. 4*a*, the metal layers 310, 312, 314, 316 of the CMOS structure each had a core metal layer 320 of Al disposed between two metal adhesion layers 302, 304 of TiW, and the CMOS dielectric 318 was $SiO_2$. In addition, intermediate metal layer 316 was also discontinuous although this is not shown in FIGS. 4*a*-4*d*. An anisotropic oxide etch, reactive ion etching with a mixture of $CHF_3$ and $O_2$ gases, was used to form channels 322 through the CMOS dielectric and down to intermediate metal layer 316 connected in series to two other metal layers 310, 312 by metal vias 308 (FIG. 4*b*). The exposed aluminum core metal layer 320 of the intermediate layer 316 was then wet etched using Transene Aluminum Etchant Type A, a mixture containing 80% phosphoric acid, 5% nitric acid, 5% acetic acid and 10% distilled water, injected into one of the channels, leaving the TiW adhesion layers 302, 304 intact (FIG. 4*c*). Photoresist (Clariant AZ-4210) was used to prevent the exposed aluminum pads (not shown) on the surface of the CMOS from being etched during this stage. The chip was rinsed in de-ionized water followed by successive rinses in acetone and methanol to prevent surface tension from pulling the capacitor plates (the TiW adhesion layers 302, 304) closed. A polymer 306 composed of polyimide (HD Microsystems PI-2556) diluted by a factor of 24:1 with a 50:50 mixture of n-methyl-2-pyrrolidone and methoxy propanol (HD Microsystems T-9039) was injected into one of the channels 322 using a custom drop-on-demand inkjet system (FIG. 4*d*). Polyimide was chosen because it is widely used for humidity sensing, allowing comparison with other sensor topologies.

Specifically as depicted in FIG. 5*b*, an 80 μm diameter channel 322*a* in the center of the structure served as a target for drops from a 60 μm inkjet nozzle. Multiple square channels 322*b* (2.6 μm on a side) served both as release holes for the aluminum etch and as access holes for water vapor to absorb into the polyimide layer. Discontinuities in the intermediate metal layer 316 resulted in CMOS dielectric pillars 326 surrounding the channel 322*a* at the center of the device, holding the top and bottom capacitor plates (TiW adhesion layers 302, 304) apart.

Figure 8:
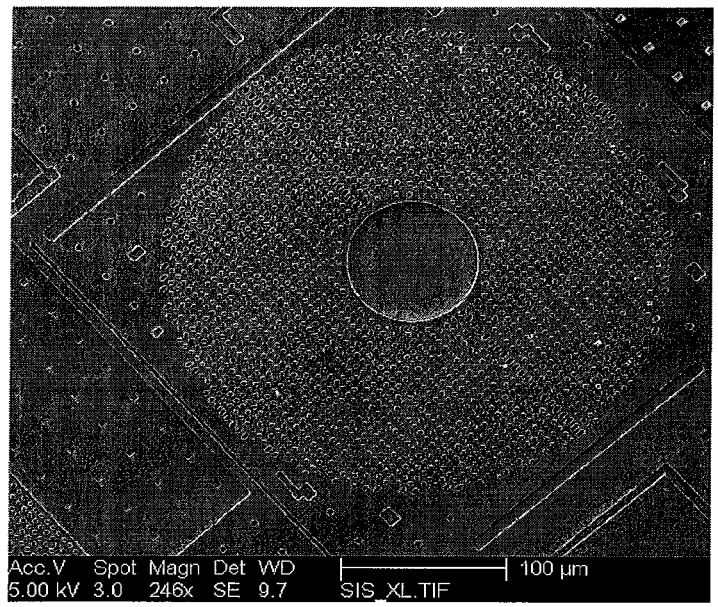
FIGS. 8a and 8b are SEM images of one embodiment of a CMOS with an integrated chemical sensor (a) before and (b) after inkjetting of polymer with an inset SEM image of filled release holes.
Figure 8:
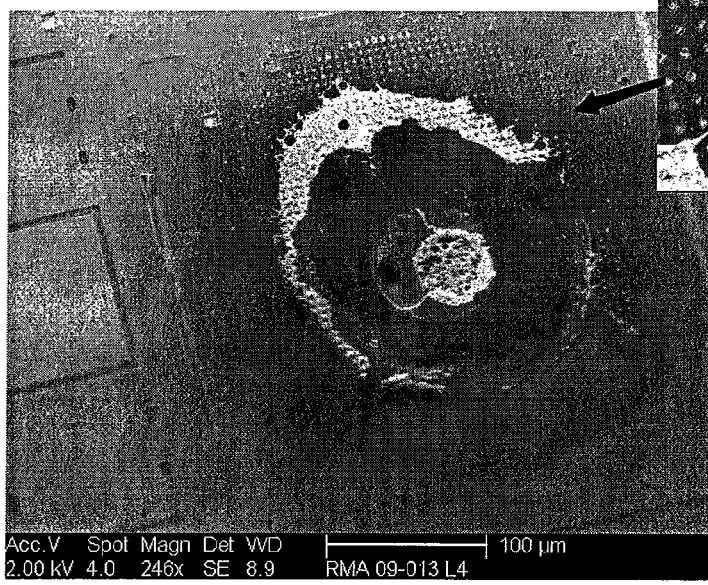
Figure 8:
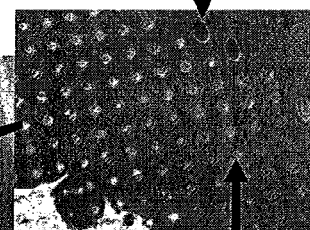

SEM photomicrographs of the surface of the CMOS before and after inkjetting of the polyimide are shown in FIGS. 8*a* and 8*b*. Because the polyimide fill could not be verified optically during inkjetting, the cavity 324 and channels 322*a*, 322*b* were deliberately overloaded, resulting in significant polymer residue on the outer surface 328 of the CMOS. This residue layer will reduce the speed of the device slightly, since water vapor will need to diffuse a longer distance into the device to reach the polymer 306 in the cavity 324. However, the process can be optimized to minimize the excess polymer and improve the response time by methods know to those skilled in the art.

Theoretical Model: To assist in understanding the described chemical sensor, information on the theoretical model that underlies the described chemical sensor is provided, with reference to its use as a humidity sensor. The humidity sensor is modeled using a parallel-plate capacitor approximation, since the gap between the electrodes (metal adhesion layers) (nominally 450 nm) is very small relative to the area of the structure. The dielectric constant for polymer with absorbed water vapor is:

$$\in = [\gamma(\in_{H_2O}^{1/3} - \in_P^{1/3}) + \in_P^{1/3}]^3 \qquad \text{Equation 1}$$

where γ is the volume fraction of water in the film, and $\in_P$ and $\in_{H_2O}$ are the dielectric constants of polymer and water, respectively (Fenner and Zdankiewicz, "Micromachined Water Vapor Sensors: A Review of Sensing Technologies", IEEE Sensors J., 2001, Vol. 1, pp. 309-317).

In this case for humidity sensing, polyimide was used due to its linear response to relative humidity. Polyimide has a volume fraction of water approximately given by (Shibata, cited in Background section):

$$\gamma = c_1 (\% \text{ RH})^{c_2} \qquad \text{Equation 2}$$

The terms $c_1$ and $c_2$ are temperature-dependent constants and % RH is the percentage of relative humidity.

The sensor is modeled as a parallel-plate capacitor, $$C = \frac{\varepsilon A}{d} \qquad \text{Equation 3}$$

where A is the area and d is the gap between the capacitor plates. This capacitance can change due to either changes in the dielectric constant according to equation 1, or due to changes in capacitor dimensions from material swelling. Polymer expansion is neglected in the humidity sensor model because the volume coefficient of expansion of polyimide is small, only 60-75 ppm/% RH.

Figure 9:
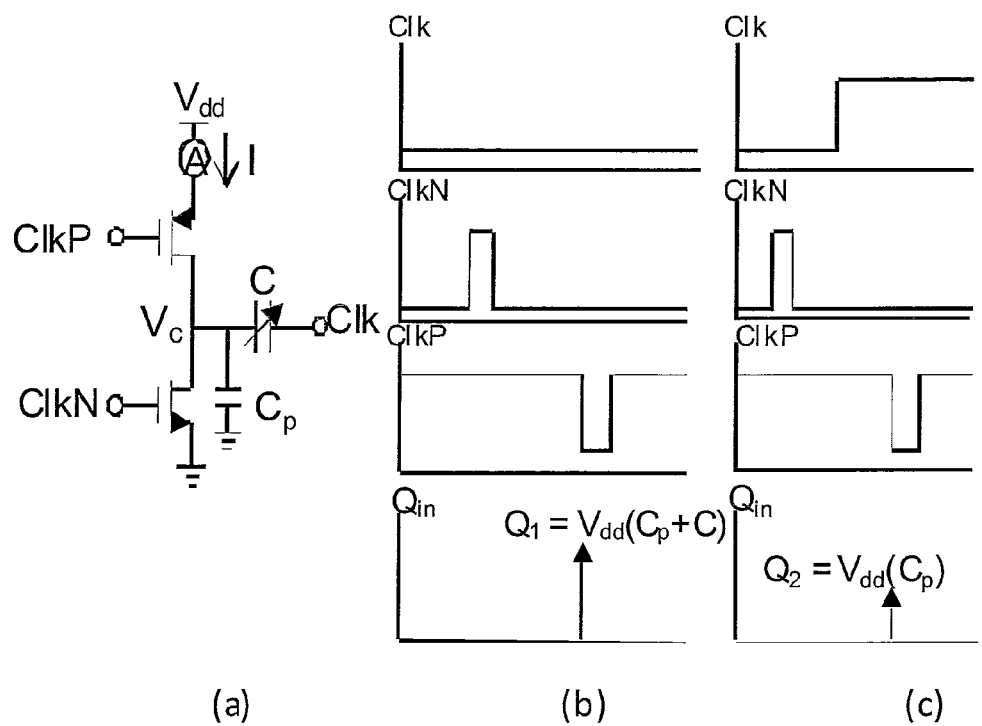
FIGS. 9a-9c are a (a) CBCM circuit, (b) a timing diagram for a first measurement and (c) a timing diagram for second measurement.

Testing Circuit: The exemplar humidity sensor using polymer polyimide was integrated on a CMOS die with a charge-based capacitance measurement (CBCM) circuit shown in FIGS. 9*a*-9*c*. Those skilled in the art will recognize that many other circuits exist to detect capacitance for a sensor, including switched capacitor circuits, integration amplifiers, transimpedance amplifiers, and high-impedance voltage preamplifiers. Likewise those skilled in the art will recognize that the capacitive sensor can be combined with one or more other capacitive sensors or fixed capacitors to form capacitive divider circuits and capacitive bridge circuits, which can improve the performance of the output offset and help reject common-mode disturbances.

This CBCM circuit uses two separate measurements to measure the sensing capacitance C and isolate it from the parasitic capacitance to ground, $C_p$. In the current design, this parasitic capacitance results from the capacitance between the top electrode plate (top metal adhesion layer) and the grounded adhesion layer left behind from the metal layer used to protect the wiring from the aluminum etch, and is approximately 10% of the size of the sensing capacitance. This capacitance may be reduced by wiring masking metal to the top electrode plate of the sensor. In the first measurement, illustrated in the timing diagram of FIG. 9b, the Clk input is grounded while the center node $V_c$ is first discharged to ground, then charged to $V_{dd}$, resulting in both the sensing capacitance C and the parasitic capacitance $C_p$ being charged. This cycle is repeated at frequency $f_s$ and measured with a DC picoammeter, resulting in the current:

$$I_1 = f_s(C+C_p)V_{dd} \quad \text{Equation 4}$$

In the second measurement (FIG. 9c), the Clk input is grounded while the center node is discharged, but brought to $V_{dd}$ when the center node is charged. Charge is only stored on the parasitic capacitance $C_p$, since there is no voltage drop across the sensing capacitor, resulting in total current:

$$I_2 = f_s C_p V_{dd} \quad \text{Equation 5}$$

The sensing capacitance is calculated as:

$$C = \frac{I_1 - I_2}{f_s V_{dd}} \quad \text{Equation 6}$$

Figure 10:
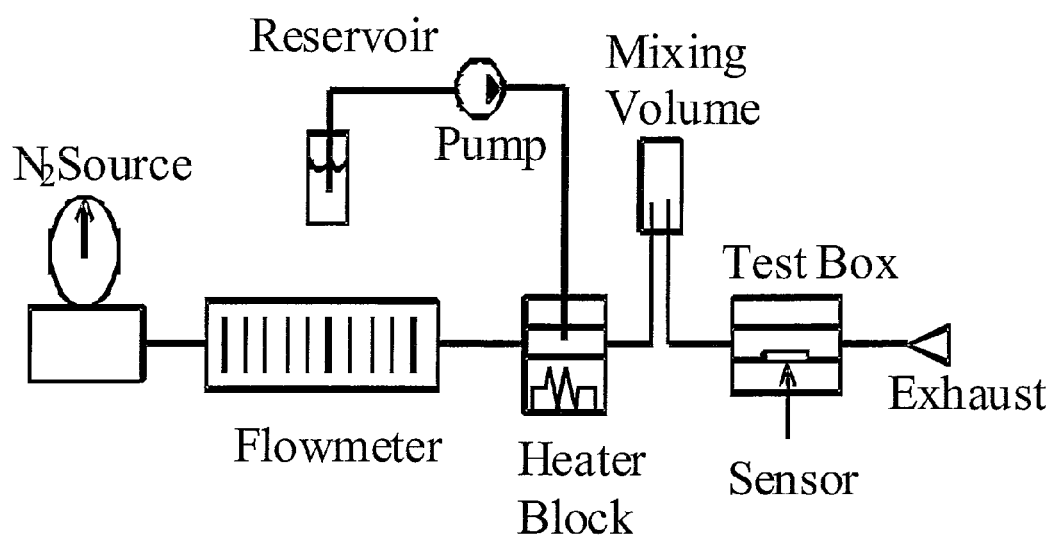
FIG. 10. shows a schematic of the humidity sensor test setup used to test the exemplary chemical sensor.

Flow System: The exemplar humidity sensor was tested using the flow system shown in FIG. 10. A Milligat M6 solvent pump pumps liquid water into a 1 L/min nitrogen flow; a brass block heated to 48° C. is used to encourage the water to vaporize. The airflow passes into a 250 mL mixing volume, and then into the test box containing the sensor. A Honeywell HIH 4000 humidity sensor in the test box is used to obtain actual reference humidity value.

Figure 11:
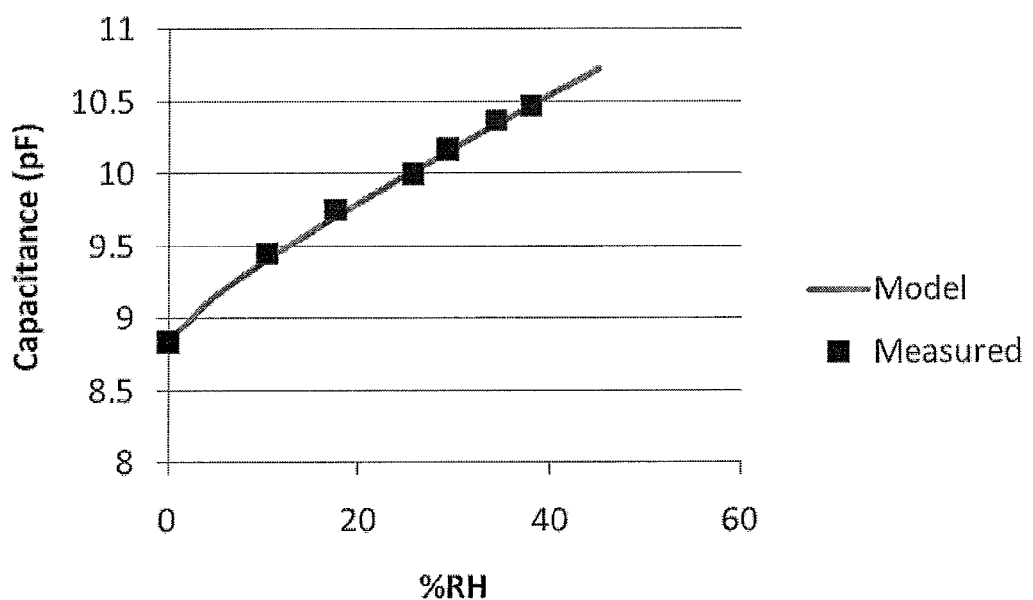
FIG. 11. is a humidity sensor response curve from testing done on the exemplary chemical sensor.

Humidity Testing: The exemplar humidity sensor using polymer polyimide was measured for a range of relative humidity from 0% to 40%, resulting in the response curve in FIG. 11. The results presented herein are representative of this embodiment, but do not represent the limits of the results that are attainable with other embodiments. The sensor response was fitted to the theoretical model for polyimide, giving an adjusted $R^2$ value of 0.9964. The sensitivity in the linear region of the sensor was fitted to be 0.31% change in capacitance per percent relative humidity. A second sensor was tested using a Miller-Nelson HCS-401 flow-temperature-humidity control system over the range from 30% to 75% relative humidity, giving a linear response with a sensitivity of 0.30%/% RH. The non-integrated polyimide vertical parallel-plate sensor presented in Dokmeci and Najafi (cited in the Background of the Art section) had a comparable sensitivity of 0.31%/% RH.

Figure 12:
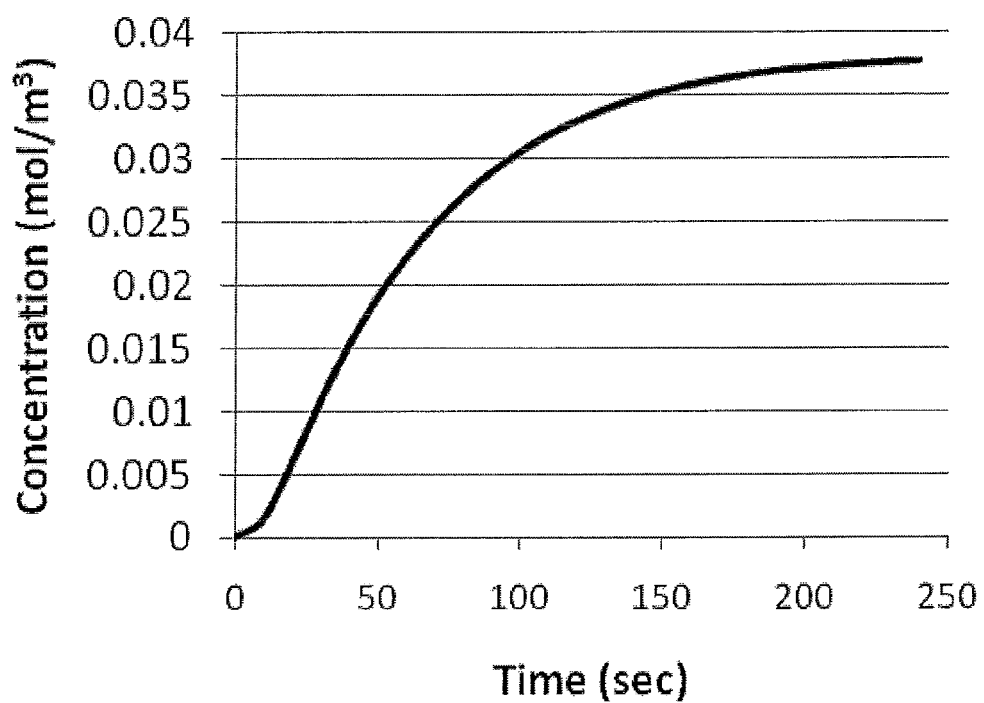
FIG. 12. is a graph showing a simulation of humidity concentration between plates in response to stepped humidity pulse.

Response Time: In the CMOS, the environment-sensitive dielectric material (polymer) wicks to the top of the channels, as shown schematically in FIGS. 5a and 5b. As a result, water vapor must diffuse through several microns of absorbing material (polymer) before reaching the area between the two metal adhesion layers that forms the actual capacitor, potentially resulting in a slow response time. Polymer deposited on the top surface will further increase this distance, slowing down the device further. The absorption of water vapor into the polymer is modeled using Fick's second law:

$$\frac{\partial c}{\partial t} = D\nabla^2 c \quad \text{Equation 7}$$

where c is the concentration of water vapor and D is the diffusion coefficient of water vapor for the specific polymer. This diffusion model was found to be accurate for relative humidity pulses up to 50%. The response time of the sensor was simulated using finite element modeling. The diffusion coefficient for water vapor in polyimide is $15 \times 10^{-14}$ m²/s. FIG. 12 shows the concentration of water vapor between the plates for a sensor having polymer to the top of the release holes for a 3% step in relative humidity, corresponding to 0.038 mol of water per cubic meter for 25° C. temperature and 1 atm pressure. The simulated time constant for the device is 68 s.

Figure 13:
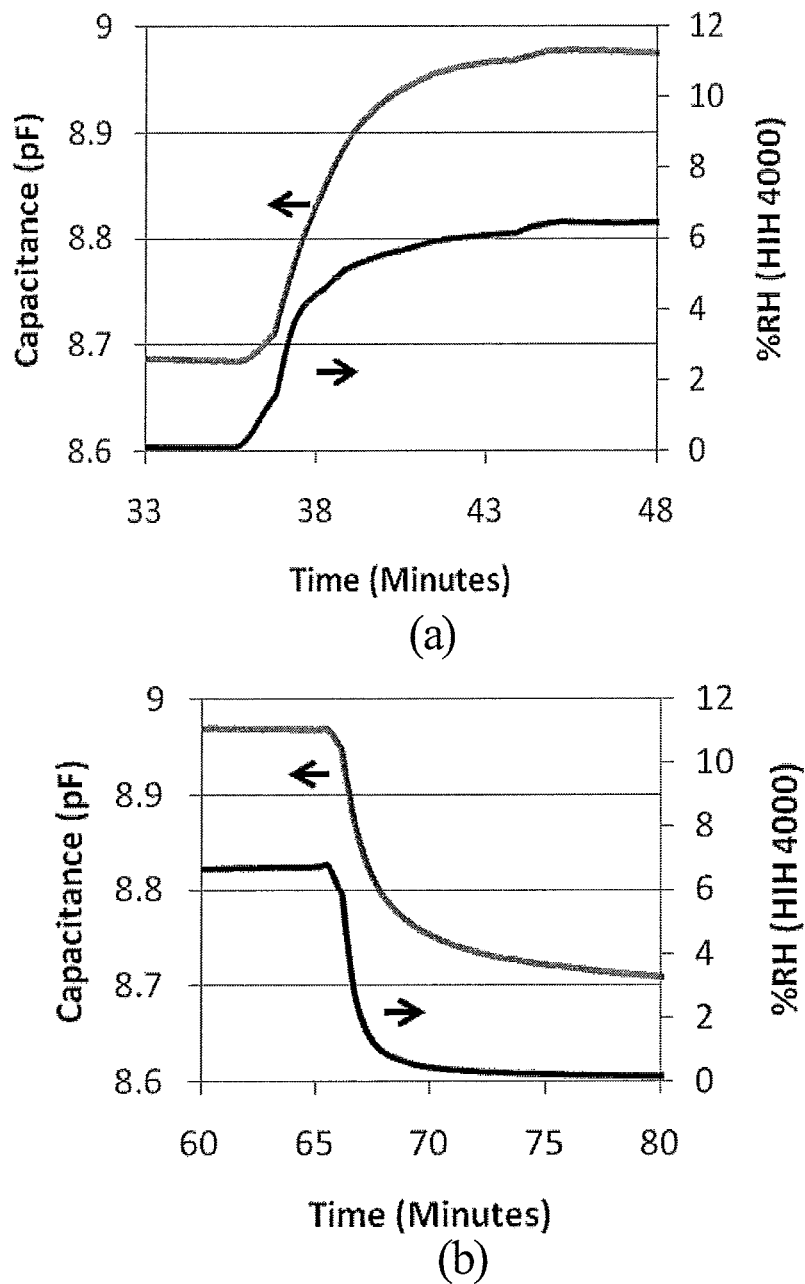
FIGS. 13a and 13b are graphs showing sensor response to humidity pulses for the exemplary chemical sensor.

To determine the actual response time of the sensor, a test was run with low concentration pulses of water vapor. The absorption (FIG. 13a) and desorption (FIG. 13b) responses of the integrated sensor to a pulse of relative humidity, along with the response of the reference sensor were determined. Unlike the simulated response, the input humidity pulse is not a sudden step; the flow system used includes a mixing volume and length of tubing that will result in a more gradual transition. However, the response time can be compared to the Honeywell reference sensor with a known time constant to changes in relative humidity of 15 s.

The measured rise and fall time constants of the integrated vertical parallel-plate sensor were both 3.16 minutes, while the Honeywell reference sensor had a rise time constant of 2.25 minutes and a fall time constant of 2.0 minutes. Although the specific polymer used in the Honeywell sensor is unknown, the desorption and absorption diffusion coefficients of polymers can be different at some concentrations, which likely causes the difference between the rise and fall times for the sensor. The response time constant of the integrated sensor is 55 s longer than the response of the reference Honeywell sensor for a rising pulse, and 70 s longer for a falling pulse. The simulation gave a response 53 s longer (68 s response time constant for the sensor simulation compared with a response of 15 s from the datasheet for the Honeywell sensor). Additional polymer on the top surface of the device, which was not included in the simulation, could account for a slightly longer measured response time.

Noise: Another important specification of a chemical sensor is the noise performance, i.e., the limit of detection or the minimum detectable concentration of analyte a chemical sensor can measure. The noise in a capacitor is typically small, unless there are a large number of charge traps in the device, so the dominant noise in the system will be from the CBCM circuit. One method for characterizing the noise response and limit of detection of a sensor is the Allan variance:

$$\sigma_C^2 = \frac{1}{M}\sum_{k=1}^{M} \frac{1}{2}(C_k - C_{k-1})^2 \quad \text{Equation 8}$$

where M is the number of samples. $C_k$ is the kth measured capacitance value, normalized by the initial capacitance $C_0$. The Allan deviation, the square root of the Allan variance, is a measure of the sample-to-sample variation of a sensor, and indicates the minimum change that can be detected. The minimum detectable change in capacitance is thus given by:

$$\Delta C = C_0 \sqrt{\sigma_C^2} \quad \text{Equation 9}$$

Figure 14:
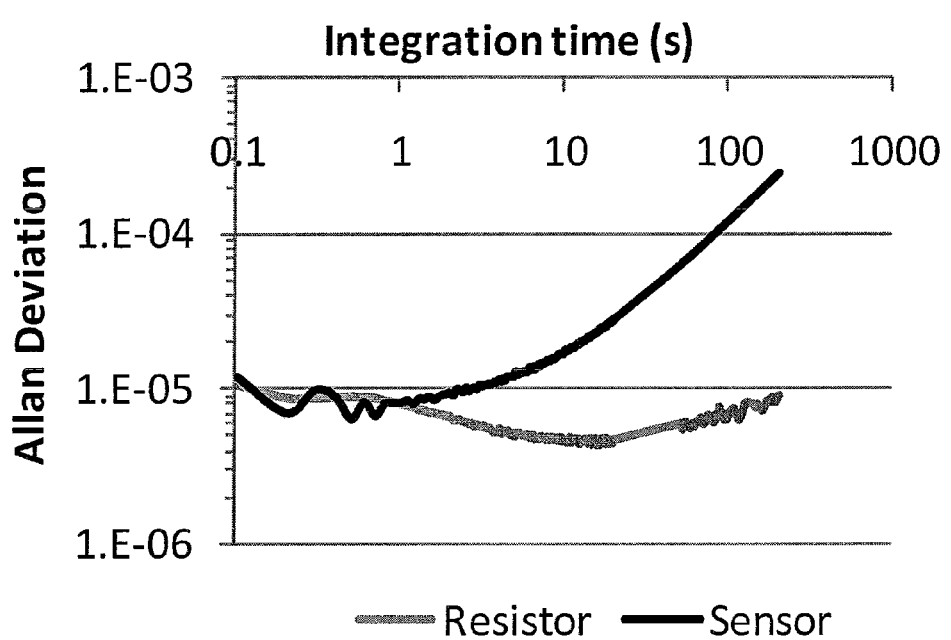
FIG. 14 is a graph showing the Allan variance of the exemplary chemical sensor integrated into a CMOS.

The Allan deviation of a system is dependent on the sampling period. Longer sampling times result in additional averaging, reducing higher frequency noise. However, for long averaging times, sensor baseline drift results in an increase in Allan deviation. FIG. 14 shows a plot of the Allan deviation of the sensor after temperature compensation for a range of sampling times. The Allan deviation of a picoammeter measurement of a comparable current through a resistor is also shown, and is an estimate of the noise level of the picoammeter. The Allan deviation is relatively flat for low integration times, approximately equal to that of the resistor; for higher integration times, sensor drift due to imperfectly compensated temperature and aging dominate, resulting in a rising Allan deviation. The lowest Allan deviation was $6.39 \times 10^{-6}$ for an averaging time of 0.5 s, corresponding to a minimum detectable signal of 0.06 fF and a limit of detection of 0.0023% change in relative humidity.

Temperature Response: The sensitivity to temperature is an important specification for a sensor that is exposed to the external environment. The temperature response was measured by using a tape heater to heat the packaged chip. Thermal grease was used to attach a thermocouple to the package near the chip to verify the chip temperature. To investigate the response of the physical structure, the thermal sensitivity was measured in a nitrogen flow to eliminate any change in capacitance due to water vapor desorbing upon a temperature change.

Figure 15:
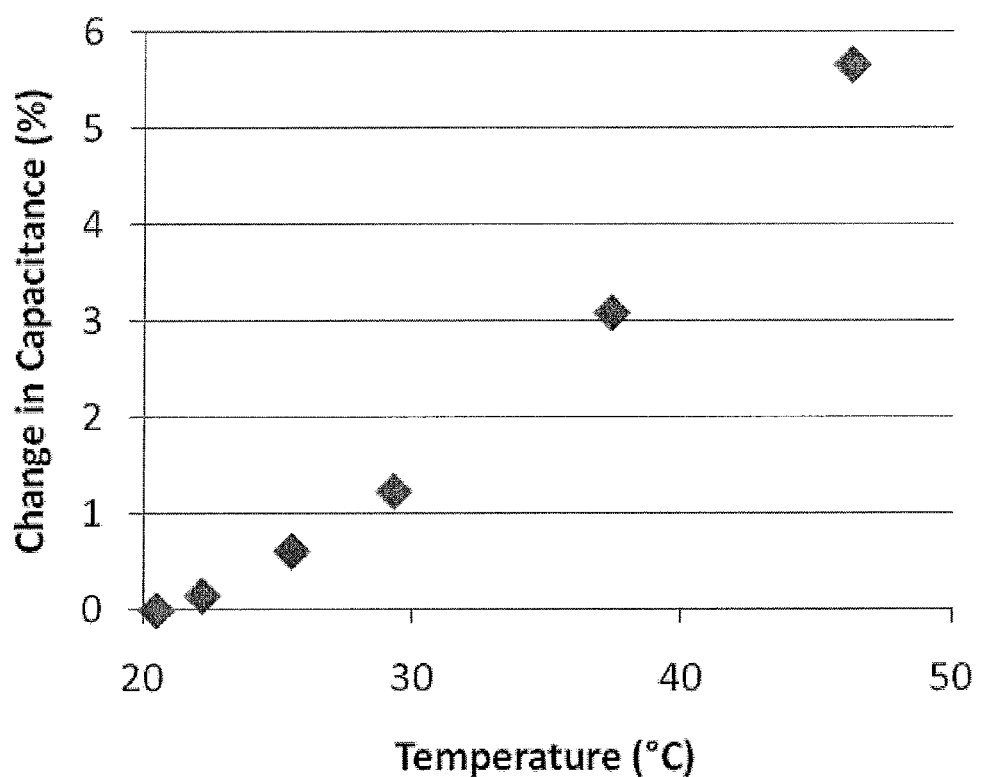
FIG. 15 is data on the temperature variance of the exemplary chemical sensor integrated into a CMOS.

FIG. 15 shows the temperature response of the sensor. The temperature sensitivity was measured to be 0.19% change in capacitance/° C. This sensitivity is relatively large, 2.7 times larger than the released interdigitated sensor with the same polymer presented in Lazarus (cited in the Background section). The high sensitivity to temperature may be because the low density of the CMOS dielectric pillars in the current structure allows the top capacitor plate to move slightly as temperature changes. Higher CMOS dielectric pillar density should hold the gap apart, reducing the thermal sensitivity.

Cross-sensitivity: This sensor may be used as part of a chemical sensor system to detect toxic industrial solvents, particularly volatile organic carbons (VOCs). As a result, cross-sensitivity to commonly used solvents is an important specification of the sensor. The sensor was tested by pumping liquid solvent into a nitrogen flow stream using the same test setup used for humidity testing. The system was calibrated using a gas chromatograph to verify the analyte concentration.

Table 1 shows the sensitivity of the humidity sensor to five volatile organic carbon vapors. Since a capacitive sensor is sensitive to the dielectric constant of absorbed analyte, three high dielectric constant alcohols (IPA, ethanol and methanol) were chosen, as well as acetone and toluene. The vapor pressure of each analyte is also listed, and reflects the volatility of the individual analyte. The largest measured response was for the highest dielectric constant analyte, methanol, with a sensitivity of $1.35 \times 10^{-4}$% change in capacitance per part per million (ppm). Although these responses are not insignificant, the sensor is designed to be used in an array of different chemical sensors, allowing techniques such as principle component analysis to be used to differentiate between chemical analytes.

TABLE 1

Material properties and sensitivity to chemicals in cross-sensitivity test

| Analyte | Dielectric Constant | Vapor Pressure at 20° C. (Pa) | Sensitivity (%/ppm) |
| --- | --- | --- | --- |
| Toluene | 2.39 | 2900 | $1.60 \times 10^{-5}$ |
| Acetone | 20.7 | 24500 | $1.80 \times 10^{-5}$ |
| IPA | 19.92 | 4340 | $7.50 \times 10^{-6}$ |
| Ethanol | 24.51 | 5850 | $5.70 \times 10^{-5}$ |
| Methanol | 32.65 | 12800 | $1.35 \times 10^{-4}$ |

To summarize the testing, the measured results for the exemplar embodiment demonstrate a vertical parallel-plate capacitive humidity sensor successfully integrated with CMOS testing electronics. The sensitivity of the sensor is 0.31%/% RH, an increase of 72% over the highest sensitivity previously demonstrated for an integrated capacitive humidity sensor (Lazarus et al., cited in the Background section). Further, the sensitivity matches the sensitivity for polyimide previously measured in a non-integrated vertical parallel-plate sensor (Patel et al., cited in the Background section). The sensor was found to be relatively slow, with a time constant on the order of a minute, since water vapor must diffuse several microns to reach the active part of the sensor. The limit of detection of the sensor was found to be 0.0023% relative humidity.

Although the present method, apparatus, and system have generally been described in terms of specific embodiments and implementations, it is not limited thereto. The examples provided herein are illustrative, and other variations and modifications are possible and contemplated. The foregoing specification is intended to cover all such modifications and variations.

We claim:

1. A capacitive environment-sensitive sensor integrated into a complementary metal oxide semiconductor (CMOS) structure, comprising a CMOS dielectric, and disposed within the CMOS dielectric:
   a first layer, comprising a metal; a second layer comprising an environment sensitive dielectric material disposed between two metal adhesion layers; and a third layer comprising a metal, wherein the second layer and two metal adhesion layers are disposed between the first and third layers, and wherein the first and third layers are connected to the two metal adhesion layers by conductive vias, thereby forming a capacitive sensor, the capacitive sensor comprising one or more passages extending from an outer surface of the capacitive sensor to the second layer.

2. The capacitive environment-sensitive sensor according to claim 1, wherein the metal adhesion layers comprise Ti, W, Ta or a combination thereof.

3. The capacitive environment-sensitive sensor according to claim 1, wherein the first and third layers comprise Al or Cu.

4. The capacitive environment-sensitive sensor according to claim 1, wherein the environment-sensitive dielectric material is a polymer.

5. The capacitive environment-sensitive sensor according to claim 1, wherein the environment-sensitive dielectric material is selected from the group consisting of: polyimide, polyisobutylene, polydimethyl siloxane, polycarbonate urethane, polyethylene-co-vinylacetate, siloxanefluoro alcohol, polyepichlorohydrine, cyanopropyl methyl phenylmethyl silicone, and dicyanoallyl silicone.

6. The capacitive environment-sensitive sensor according to claim 1, further comprising additional electronic circuitry for capacitive measurement within the CMOS structure.

7. An environment sensing system, comprising:
   one or more capacitive environment sensors integrated into a complementary metal oxide semiconductor (CMOS)

structure, each of the environment sensors independently comprising a CMOS dielectric and disposed within the CMOS dielectric: a first layer, comprising a metal; a second layer comprising an environment sensitive dielectric material disposed between two metal adhesion layers; and a third layer comprising a metal, wherein the second layer and two metal adhesion layers are disposed between the first and third layers, and wherein the first and third layers are connected to the metal adhesion layers by conductive vias, thereby forming a capacitive sensor, the capacitive sensor comprising one or more passages extending from an outer surface of the sensor to the second layer, wherein the one or more capacitive environment sensors are integrated into circuitry for capacitance measurement.

8. The environment sensing system of claim 7, wherein the circuitry for capacitance measurement is a charge-based capacitance measurement circuit.

9. The environment sensing system of claim 7, wherein the CMOS structure further comprises at least a portion of the circuitry for capacitance measurement.

10. The capacitive environment-sensitive sensor of claim 1, wherein the first layer is on a portion of the CMOS dielectric, and another portion of the CMOS dielectric is on the third layer.

11. The environment sensing system of claim 7, wherein the first layer is on a portion of the CMOS dielectric, and another portion of the CMOS dielectric is on the third layer.

12. The capacitive environment-sensitive sensor of claim 1, wherein the one or more passages extend through from the outer surface of the capacitive sensor through the CMOS dielectric to the second layer.

13. The environment sensing system of claim 7, wherein the one or more passages extend through from the outer surface of the sensor through the CMOS dielectric to the second layer.

14. A capacitive environment-sensitive sensor integrated into a complementary metal oxide semiconductor (CMOS) structure, comprising a CMOS dielectric, and disposed within the CMOS dielectric:
a first layer, wherein the first layer is metal;
a first portion of the CMOS dielectric on the first layer; a second layer on the first portion of the CMOS dielectric and connected to the first layer by a conductive via, the second layer comprising an environment sensitive dielectric material and two metal adhesion layers, wherein the environment-sensitive dielectric material is disposed between the two metal adhesion layers; a second portion of the CMOS dielectric on the second layer; and a third layer on the second portion of the CMOS dielectric and connected to the second layer by another conductive via, wherein the third layer is metal, and wherein the second layer and two metal adhesion layers are disposed between the first and third layers, and wherein the first and third layers are electrically connected to the two metal adhesion layers through conductive vias formed in the CMOS dielectric, producing a capacitive sensor; and one or more passages extending from an outer surface of the capacitive sensor to the second layer.

15. The capacitive environment-sensitive sensor of claim 14, wherein the first layer is on a third portion of the CMOS dielectric, and a fourth portion of the CMOS dielectric is on the third layer.

16. The capacitive environment-sensitive sensor of claim 14, wherein the one or more passages extend through from the outer surface of the capacitive sensor through the CMOS dielectric to the second layer.

17. The capacitive environment-sensitive sensor of claim 1, wherein the one or more passages are filled with the environment-sensitive dielectric material.

* * * * *

UNITED STATES PATENT AND TRADEMARK OFFICE
CERTIFICATE OF CORRECTION

PATENT NO.        : 8,471,304 B2                                Page 1 of 1
APPLICATION NO.   : 13/152450
DATED             : June 25, 2013
INVENTOR(S)       : Gary Keith Fedder et al.

It is certified that error appears in the above-identified patent and that said Letters Patent is hereby corrected as shown below:

On Title Page 2, Column 1, item 56, OTHER PUBLICATIONS, Line 6, delete "Microelctromechanical" and insert -- Microelectromechanical --

Signed and Sealed this
Twenty-fourth Day of December, 2013

Margaret A. Focarino
*Commissioner for Patents of the United States Patent and Trademark Office*